US006566109B2

(12) United States Patent
Kawase et al.

(10) Patent No.: US 6,566,109 B2
(45) Date of Patent: May 20, 2003

(54) GENE FOR THERMOSTABLE GLUCOKINASE, RECOMBINANT VECTOR CONTAINING THE SAME, TRANSFORMANT CONTAINING THE RECOMBINANT VECTOR AND PROCESS FOR PRODUCING THERMOSTABLE GLUCOKINASE USING THE TRANSFORMANT

(75) Inventors: Shido Kawase, Kyoto (JP); Keisuke Kurosaka, Kyoto (JP)

(73) Assignee: Unitika Ltd., Hyogo (JP)

( * ) Notice: Subject to any disclaimer, the term of this patent is extended or adjusted under 35 U.S.C. 154(b) by 0 days.

(21) Appl. No.: 10/043,238

(22) Filed: Jan. 14, 2002

(65) Prior Publication Data

US 2002/0110863 A1 Aug. 15, 2002

(30) Foreign Application Priority Data

Jan. 15, 2001 (JP) ...................... P.2001-006391

(51) Int. Cl.[7] ................................ C12N 1/20
(52) U.S. Cl. ...................... 435/194; 536/23 R
(58) Field of Search ............... 435/194, 252.33, 435/320.1; 536/23.2

(56) References Cited

U.S. PATENT DOCUMENTS 4,331,762 A    5/1982    Nakajima et al.

FOREIGN PATENT DOCUMENTS

| EP | 0 029 976 A1 | 6/1981 |
| JP | 56-127086 | 10/1981 |
| JP | 60-102195 | 6/1985 |
| JP | 61-124390 | 6/1986 |
| JP | 6-292485 | 10/1994 |
| JP | 8-508398 | 9/1996 |
| JP | 10-505498 | 6/1998 |
| JP | 10-507084 | 7/1998 |
| JP | 10-512762 | 12/1998 |
| JP | 11-127880 | 5/1999 |
| WO | WO 98/12343 | 3/1998 |

OTHER PUBLICATIONS

Christine Spath et al., Contribution of Glucose Kinase to Glucose Repression of Xylose Utilization in *Bacillus megaterium*, Journal of Bacteriology, Dec. 1997, pp. 7603–7605.
Pierre Skarlatos et al., The Glucose Kinase of *Bacillus subtilis*, Journal of Bacteriology, Jun. 1998, pp. 3222–3226.
XP–001069820, H. Hengartner et al., "Isolation and Characterization of a Thermophilic Glucokinase from *Bacillus stearothermophilus*", (1973), FEBS Letters vol. 37, No. 2, pp. 212–216.
XP–001069933, K. Tomita et al., "Thermostable Glucokinase from *Bacillus stearothermophilus* and Its Analytical Appln.", Annals New York Academy of Sciences, (1990) pp. 421–425.
XP–001069023, B. French et al., "High–Level Expression of *Bacillus stearothermophilus* 6–phosphofructo–1–Kinase in *Escherichia coli*," (1987), Gene, vol. 59, No. 2–3, pp. 279–284.
XP–002196931, Abstract of C. Spaeth et al., *Bacillus megaterium* Glk Gene (1997), J. Bacteriology, vol. 179, No. 23.
European Search Report dated May 22, 2002.

*Primary Examiner*—Ponnathapu Achutamurthy
*Assistant Examiner*—Malgorzata A. Walicka
(74) *Attorney, Agent, or Firm*—Sughrue Mion, PLLC

(57) ABSTRACT

A gene encoding thermostable glucokinase, a recombinant vector comprising this gene, a transformant transformed with the recombinant vector, and a process for producing thermostable glucokinase with the use of the transformant.

8 Claims, 1 Drawing Sheet

SEQUENCE LISTING

<160> NUMBER OF SEQ ID NOS: 6

<210> SEQ ID NO 1
<211> LENGTH: 317
<212> TYPE: PRT
<213> ORGANISM: Bacillus stearothermophilus UK-563

<400> SEQUENCE: 1

```
Met Glu Gln Trp Leu Val Gly Ile Asp Leu Gly Thr Thr Thr Lys
1               5                   10                  15

Met Ala Phe Ile Thr Glu Asp Gly Ile Ile Val His Lys Trp Glu Ile
                20                  25                  30

Pro Thr Asp Thr Ser Asn Arg Gly Glu Arg Ile Val Ala His Ile Ala
            35                  40                  45

Arg Ser Leu Asp Glu Thr Leu Ala Arg Leu Gly Thr Lys Glu Gln
        50                  55                  60

Leu Leu Ala Ile Gly Ile Gly Ala Pro Gly Pro Val Gln Glu Glu Thr
65                  70                  75                  80

Gly Met Leu Tyr Glu Ala Val Asn Leu Gly Trp Lys His Tyr Pro Leu
                85                  90                  95

Lys Arg Gln Leu Glu Glu Thr Gly Leu Pro Val Ala Val Asp Asn
            100                 105                 110

Asp Ala Asn Ile Ala Ala Leu Gly Glu Met Trp Lys Gly Ala Gly Gly
            115                 120                 125

Gly Ala Arg His Leu Leu Phe Val Thr Leu Gly Thr Gly Val Gly Gly
        130                 135                 140

Gly Val Ile Ala Asn Gly Ala Ile Val Arg Gly Thr Asn Gly Ala Gly
145                 150                 155                 160

Gly Glu Ile Gly His Met Thr Met Val Ala Asp Gly Gly Ala Pro Cys
                165                 170                 175

Asn Cys Gly Lys Thr Gly Cys Leu Glu Thr Ile Ala Ser Ala Thr Gly
            180                 185                 190

Ile Val Arg Ile Ala Gly Glu Lys Leu Ala Ala Ser Glu Arg Pro Ser
        195                 200                 205

Ala Leu Arg Gly Gly Asp Val Thr Ala Lys Ala Val Phe Asp Ala Ala
    210                 215                 220

Lys Thr Gly Asp Ala Leu Ala Leu Glu Val Val Glu Glu Val Thr Arg
225                 230                 235                 240

Tyr Leu Gly Leu Ala Leu Ala Asn Ala Ala Asn Val Thr Asn Pro Glu
                245                 250                 255

Lys Ile Val Ile Gly Gly Val Ser Lys Ala Gly Ala Leu Leu Val
            260                 265                 270

Glu His Val Ala Ala His Phe Arg Arg Tyr Ala Phe Pro Arg Val Ala
        275                 280                 285

Ala Gly Ala Glu Ile Val Leu Ala Thr Leu Gly Asn Asp Ala Gly Val
    290                 295                 300

Ile Gly Gly Ala Trp Leu Ala Lys Ser Leu Ile Gly Ala
305                 310                 315
```

<210> SEQ ID NO 2
<211> LENGTH: 954
<212> TYPE: DNA
<213> ORGANISM: Bacillus stearothermophilus UK-563
<220> FEATURE:
<221> NAME/KEY: CDS

```
<222> LOCATION: (1)..(954)

<400> SEQUENCE: 2 atg gaa cag tgg ttg gtg ggc atc gat ctt ggc ggc acg acg aag        48
Met Glu Gln Trp Leu Val Gly Ile Asp Leu Gly Gly Thr Thr Thr Lys
1               5                   10                  15 atg gcg ttt att aca gaa gac gga att att gta cac aaa tgg gaa att    96
Met Ala Phe Ile Thr Glu Asp Gly Ile Ile Val His Lys Trp Glu Ile
            20                  25                  30 cca aca gac acg tcc aac cgc ggc gaa cgg atc gtc gcc cat atc gcc   144
Pro Thr Asp Thr Ser Asn Arg Gly Glu Arg Ile Val Ala His Ile Ala
        35                  40                  45 cgg tcg ttg gat gaa acg ctc gcc cgg ctt ggc gga acg aaa gaa cag   192
Arg Ser Leu Asp Glu Thr Leu Ala Arg Leu Gly Gly Thr Lys Glu Gln
    50                  55                  60 ctg ctc gcc atc gga atc ggc gcc ccc ggg ccg gtt cag gaa gaa aca   240
Leu Leu Ala Ile Gly Ile Gly Ala Pro Gly Pro Val Gln Glu Glu Thr
65                  70                  75                  80 gga atg ctg tat gaa gcg gtc aat cta gga tgg aaa cac tac ccc tta   288
Gly Met Leu Tyr Glu Ala Val Asn Leu Gly Trp Lys His Tyr Pro Leu
                85                  90                  95 aaa cga cag ctc gaa gaa gag aca ggg ctg ccg gtg gcc gtc gac aat   336
Lys Arg Gln Leu Glu Glu Glu Thr Gly Leu Pro Val Ala Val Asp Asn
            100                 105                 110 gac gcg aat atc gcc gcc ctc ggc gaa atg tgg aaa ggg gcc ggg gga   384
Asp Ala Asn Ile Ala Ala Leu Gly Glu Met Trp Lys Gly Ala Gly Gly
        115                 120                 125 ggg gcg cgc cat ttg ctg ttt gtg acg ctc ggc acc ggc gtt ggc ggc   432
Gly Ala Arg His Leu Leu Phe Val Thr Leu Gly Thr Gly Val Gly Gly
    130                 135                 140 ggc gta atc gcc aac ggg gcc atc gtg cgc ggg acg aac ggc gcc ggt   480
Gly Val Ile Ala Asn Gly Ala Ile Val Arg Gly Thr Asn Gly Ala Gly
145                 150                 155                 160 gga gaa atc ggc cat atg acg atg gtt gca gac ggc ggc gcg ccg tgc   528
Gly Glu Ile Gly His Met Thr Met Val Ala Asp Gly Gly Ala Pro Cys
                165                 170                 175 aac tgc ggc aaa acg ggc tgt ttg gaa acg att gcg tcg gcg acc ggc   576
Asn Cys Gly Lys Thr Gly Cys Leu Glu Thr Ile Ala Ser Ala Thr Gly
            180                 185                 190 att gtg cgg att gcc ggc gaa aag ctg gct gcc agc gag cgt ccg agc   624
Ile Val Arg Ile Ala Gly Glu Lys Leu Ala Ala Ser Glu Arg Pro Ser
        195                 200                 205 gcg ctc cgc ggc ggc gat gtc acc gcc aaa gct gtg ttt gac gcc gcc   672
Ala Leu Arg Gly Gly Asp Val Thr Ala Lys Ala Val Phe Asp Ala Ala
    210                 215                 220 aaa acg ggg gat gcg ctc gcg ctt gag gtt gtt gag gag gtg acg cgc   720
Lys Thr Gly Asp Ala Leu Ala Leu Glu Val Val Glu Glu Val Thr Arg
225                 230                 235                 240 tat ctc ggt ttg gcg ttg gcg aat gcg gct aat gtg acc aat ccg gag   768
Tyr Leu Gly Leu Ala Leu Ala Asn Ala Ala Asn Val Thr Asn Pro Glu
                245                 250                 255 aaa att gtg atc ggc ggc ggt gtc tcg aag gcg ggg gca ctg ctc gtt   816
Lys Ile Val Ile Gly Gly Gly Val Ser Lys Ala Gly Ala Leu Leu Val
            260                 265                 270 gag cat gtc gcc gcc cat ttc cgc cgc tat gct ttt ccg cgt gtc gcc   864
Glu His Val Ala Ala His Phe Arg Arg Tyr Ala Phe Pro Arg Val Ala
        275                 280                 285 gcc gga gcg gag atc gtg ctg gca acg ctc ggc aat gac gcc gga gtc   912
Ala Gly Ala Glu Ile Val Leu Ala Thr Leu Gly Asn Asp Ala Gly Val
    290                 295                 300
```

```
atc ggc ggc gcc tgg ttg gcg aaa tcg ctc atc ggc gcc taa          954
Ile Gly Gly Ala Trp Leu Ala Lys Ser Leu Ile Gly Ala
305                 310                 315
```

<210> SEQ ID NO 3
<211> LENGTH: 317
<212> TYPE: PRT
<213> ORGANISM: Bacillus stearothermophilus UK-563

<400> SEQUENCE: 3

```
Met Glu Gln Trp Leu Val Gly Ile Asp Leu Gly Thr Thr Thr Lys
1               5                   10                  15

Met Ala Phe Ile Thr Glu Asp Gly Ile Ile Val His Lys Trp Glu Ile
                20                  25                  30

Pro Thr Asp Thr Ser Asn Arg Gly Glu Arg Ile Val Ala His Ile Ala
                35                  40                  45

Arg Ser Leu Asp Glu Thr Leu Ala Arg Leu Gly Gly Thr Lys Glu Gln
        50                  55                  60

Leu Leu Ala Ile Gly Ile Gly Ala Pro Gly Pro Val Gln Glu Glu Thr
65                  70                  75                  80

Gly Met Leu Tyr Glu Ala Val Asn Leu Gly Trp Lys His Tyr Pro Leu
                85                  90                  95

Lys Arg Gln Leu Glu Glu Thr Gly Leu Pro Val Ala Val Asp Asn
                100                 105                 110

Asp Ala Asn Ile Ala Ala Leu Gly Glu Met Trp Lys Gly Ala Gly Gly
                115                 120                 125

Gly Ala Arg His Leu Leu Phe Val Thr Leu Gly Thr Gly Val Gly Gly
        130                 135                 140

Gly Val Ile Ala Asn Gly Ala Ile Val Arg Gly Thr Asn Gly Ala Gly
145                 150                 155                 160

Gly Glu Ile Gly His Met Thr Met Val Ala Asp Gly Ala Pro Cys
                165                 170                 175

Asn Cys Gly Lys Thr Gly Cys Leu Glu Thr Ile Ala Ser Ala Thr Gly
                180                 185                 190

Ile Val Arg Ile Ala Gly Glu Lys Leu Ala Ala Ser Glu Arg Pro Ser
                195                 200                 205

Ala Leu Arg Gly Gly Asp Val Thr Ala Lys Ala Val Phe Asp Ala Ala
        210                 215                 220

Lys Thr Gly Asp Ala Leu Ala Leu Glu Val Val Glu Glu Val Thr Arg
225                 230                 235                 240

Tyr Leu Gly Leu Ala Leu Ala Asn Ala Ala Asn Val Thr Asn Pro Glu
                245                 250                 255

Lys Ile Val Ile Gly Gly Val Ser Lys Ala Gly Ala Leu Leu Val
                260                 265                 270

Glu His Val Ala Ala His Phe Arg Arg Tyr Ala Phe Pro Arg Val Ala
        275                 280                 285

Ala Gly Ala Glu Ile Val Leu Ala Thr Leu Gly Asn Asp Ala Gly Val
        290                 295                 300

Ile Gly Gly Ala Trp Leu Ala Lys Ser Leu Ile Gly Ala
305                 310                 315
```

<210> SEQ ID NO 4
<211> LENGTH: 23
<212> TYPE: DNA
<213> ORGANISM: Artificial Sequence
<220> FEATURE:

```
<223> OTHER INFORMATION: Synthesized DNA
<221> NAME/KEY: misc_feature
<222> LOCATION: (15)..(15)
<223> OTHER INFORMATION: n = G, A, T or C
<221> NAME/KEY: misc_feature
<222> LOCATION: (18)..(18)
<223> OTHER INFORMATION: n = G, A, T or C
<221> NAME/KEY: misc_feature
<222> LOCATION: (21)..(21)
<223> OTHER INFORMATION: n = G, A, T or C

<400> SEQUENCE: 4
atggarcart ggmtngtngg nat                                          23

<210> SEQ ID NO 5
<211> LENGTH: 23
<212> TYPE: DNA
<213> ORGANISM: Artificial Sequence
<220> FEATURE:
<223> OTHER INFORMATION: Synthesized DNA
<221> NAME/KEY: misc_feature
<222> LOCATION: (6)..(6)
<223> OTHER INFORMATION: n = G, A, T or C
<221> NAME/KEY: misc_feature
<222> LOCATION: (9)..(9)
<223> OTHER INFORMATION: n = G, A, T or C

<400> SEQUENCE: 5
gtrtcngtng gdatytccca ytt                                          23

<210> SEQ ID NO 6
<211> LENGTH: 85
<212> TYPE: DNA
<213> ORGANISM: Artificial Sequence
<220> FEATURE:
<223> OTHER INFORMATION: Synthesized DNA

<400> SEQUENCE: 6
ccatggaaca gtggctggtt ggcatcgacc tgggcggcac caccaccaaa atggcgttca   60
tcaccgaaga cggcatcatt gtaca                                        85
```

GENE FOR THERMOSTABLE GLUCOKINASE, RECOMBINANT VECTOR CONTAINING THE SAME, TRANSFORMANT CONTAINING THE RECOMBINANT VECTOR AND PROCESS FOR PRODUCING THERMOSTABLE GLUCOKINASE USING THE TRANSFORMANT

FIELD OF THE INVENTION

The present invention relates to a gene (polynucleotide) encoding a thermostable glucokinase, a recombinant vector comprising this gene, a transformant transformed with the recombinant vector, and a process for producing a thermostable glucokinase through the use of the transformant.

BACKGROUND OF THE INVENTION

Glucokinase [EC.2.7.1.2] is an enzyme which plays an important role in vivo in the first step of the glycolytic pathway, i.e. introduction of ATP. It is also an industrially useful enzyme and it is employed in various test reagents that are used for measuring whether glucose is in a test composition and in the consumption of glucose in a sample.

Glucokinase shows a very high substrate specificity for glucose. Hexokinase [EC.2.7.1.1], which is known as an enzyme that catalyzes similar reactions, is a different enzyme that acts upon various saccharides as substrates. These two enzymes are also differ from each other in that they show low amino acid sequence homology.

The present inventors have found that glucokinase isolated from *Bacillus stearothermophilus*, which is a thermophilic microorganism, is highly stable and they have proposed a process for efficiently producing the same (Japanese Patent Application Laid-Open No. 127086/1981).

There have been reported other methods of expressing glucokinase genes in vivo such as in Japanese Patent Application Laid-Open No. 102195/1985, Japanese Patent Application Laid-Open No. 124390/1986, Japanese Patent Application Laid-Open No. 127880/1999, Published Japanese Translation of International Patent Publication No. 512762/1998, Japanese Patent Application Laid-Open No. 292485/1994, Published Japanese Translation of International Patent Publication No. 507084/1998, Published Japanese Translation of International Patent Publication No. 505498/1998, Published Japanese Translation of International Patent Publication No. 508398/1996, Domestic Re-publication of International Patent Publication No. 012343/1998, etc. However, the glucokinases disclosed in these publications are different from the enzyme described in the present invention in the points of stability, affinity for substrate, etc. In addition, the expression methods disclosed therein are not suitable for the large scale production through the isolation and purification and, therefore, are different from the process disclosed in the present invention.

SUMMARY OF THE INVENTION

The above-mentioned production process proposed by the present inventors makes it possible to obtain a glucokinase having a high heat stability and an excellent storage stability, and to easily purify the enzyme. However, much energy is needed in producing a thermostable glucokinase by the above-mentioned process, since the microorganism is cultured at a high temperature of generally 50 to 60° C. In addition, there still remains an unsolved problem that this microorganism can produce glucokinase only in a small amount and thus it is difficult to produce glucokinase on a large scale.

The present invention aims at providing a gene manipulation material for genetic engineeringly producing thermostable glucokinase originating from a thermophilic microorganism *Bacillus stearothermophilus* in a large amount, and a process for producing thermostable glucokinase through the use of this material.

To meet these goals, the present inventors have conducted extensive studies and, as a result, succeeded in the isolation of a gene for thermostable glucokinase produced by the above-described *Bacillus stearothermophilus* and in the determination of the structure thereof. Furthermore, they have prepared a recombinant vector having the gene encoding thermostable glucokinase inserted into a vector DNA and shown that the thermostable glucokinase can be efficiently produced by culturing a bacterial strain capable of producing the thermostable glucokinase. The bacterial strain was constructed by introducing the recombinant vector into a strain belonging to, for example, the genus Escherichia, in a medium and the like, thereby completing the present invention.

Accordingly, the first embodiment of the present invention relates to a gene encoding thermostable glucokinase which comprises the amino acid sequence represented by SEQ ID NO:1, or a gene encoding thermostable glucokinase which comprises an amino acid sequence derived from the amino acid sequence represented by SEQ ID NO:1 by the deletion, substitution or addition of one or several amino acids.

The second embodiment of the present invention relates to a gene encoding thermostable glucokinase which has a DNA comprising the base sequence represented by SEQ ID NO:2, or a gene encoding thermostable glucokinase which comprises a base sequence derived from the base sequence represented by SEQ ID NO:2 by the deletion, substitution or addition of one or several bases.

Further, the third embodiment of the present invention relates to a recombinant vector comprising a gene according to the first or second embodiment of the present invention.

The fourth embodiment of the present invention relates to a transformant comprising the recombinant vector of the third embodiment of the present invention.

The fifth embodiment of the present invention relates to a process for producing thermostable glucokinase, which comprises culturing the transformant according to the fourth embodiment of the present invention in a medium and collecting the thermostable glucokinase from the culture.

DETAILED DESCRIPTION OF THE INVENTION

Figure 1:
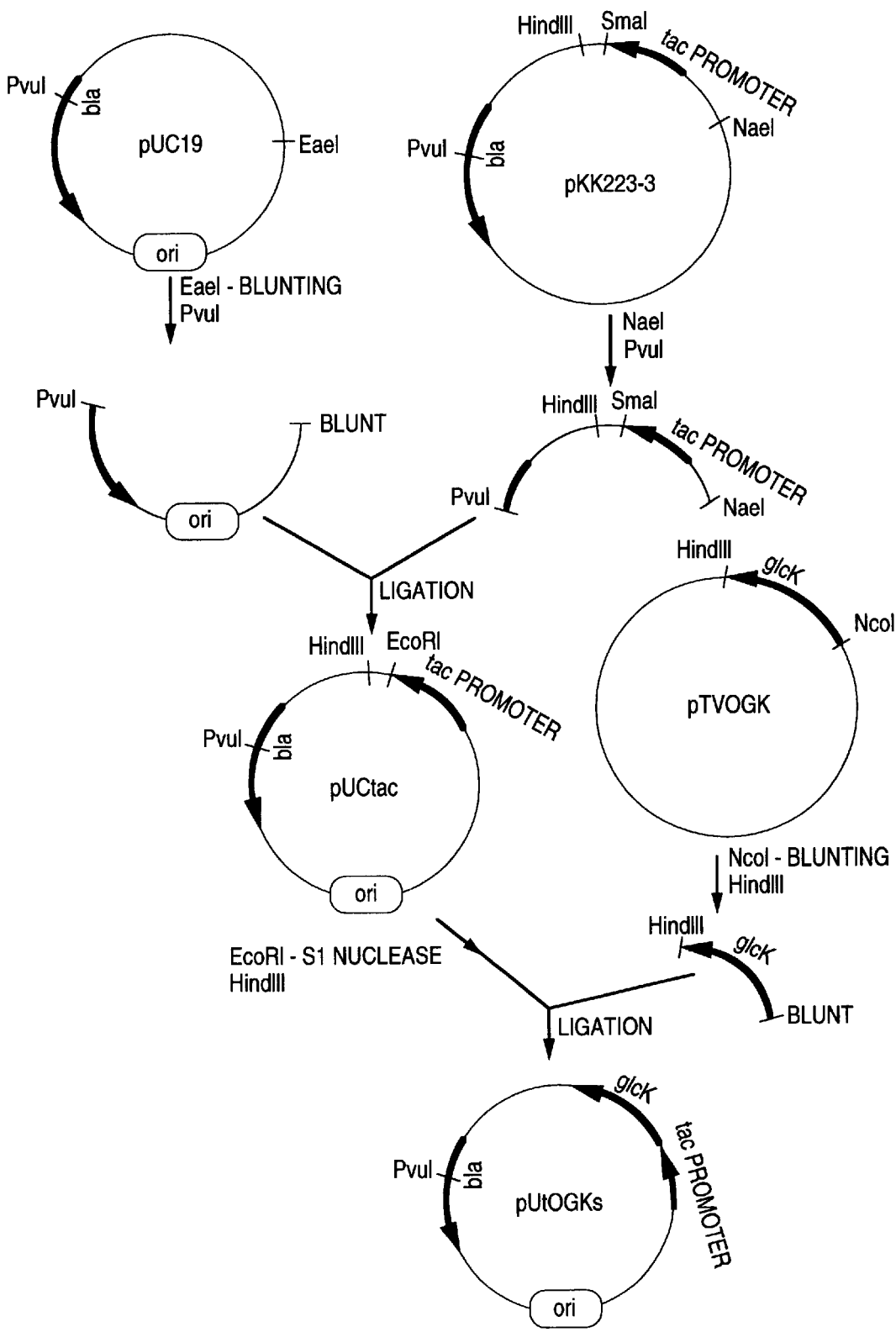
FIG. 1 is a conceptual view showing the construction of a recombinant vector containing the thermostable glucokinase gene according to the present invention.

The thermostable glucokinase according to the present invention is a protein having the amino acid sequence represented by SEQ ID NO:1. Moreover, proteins having amino acid sequences derived from this amino acid sequence by the deletion, substitution or addition of one or more amino acids are also included in the scope thereof, as long as such proteins maintain the glucokinase activity.

The genes (polynucleotide) according to the present invention are genes encoding the above-described amino acid sequence. More particularly, these genes are typified by a DNA comprising the base sequence represented by SEQ ID NO:2 or, in some cases, a gene comprising a base sequence derived from the base sequence represented by SEQ ID NO:2 by the deletion, substitution or addition of one or more bases.

In other words, the gene encoding the object enzyme of the present invention includes a polynucleotide which encodes a polypeptide having the amino acid sequence of SEQ ID NO:1, wherein one or more amino acid residues of the amino acid sequence may be modified by at least one of deletion, addition, insertion and substitution, a gene which hybridizes with said polynucleotide or the polynucleotide of SEQ ID NO:2 under stringent conditions, a polynucleotide which has homology with said polynucleotide and a polynucleotide which is degenerate with respect to said polynucleotide are also included in the present invention, with the proviso that the polypeptides encoded thereby have the enzyme activity of the present invention.

The number of deletions, additions, insertions and/or substitutions is not particularly limited as long as the enzyme activity of the thermostable glucokinase of the present invention is not lost. The number of deletions, additions, insertions and/or substitutions of the polypeptide is preferably from 1 to 20, more preferably from 1 to 10, and most preferably from 1 to 5. The number of deletions, additions, insertions and/or substitutions of the polynucleotide is preferably from 1 to 60, more preferably from 1 to 30, and most preferably from 1 to 15.

The term "under stringent conditions" as used herein means, for example, the following conditions. That is, 6×SSC, 1.0% blocking agent, 0.1% N-lauroylsarcosine sodium, 0.02% SDS.

Such a gene can be obtained by, for example, by a method wherein a partial sequence of SEQ-ID NO:2 is synthesized and then the target gene is isolated from a DNA library by using this synthetic DNA as a probe, or the PCR method wherein the target gene is amplified by using synthetic DNAs of both terminal parts of SEQ ID NO:2 as primers and a chromosomal DNA as a template.

As a microorganism providing the thermostable glucokinase according to the present invention, it is adequate to use thermophilic microorganisms belonging to the genus Bacillus, in particular, *Bacillus stearothermophilus*. Particular examples thereof include UK-563 (FERM P-7275), ACTT-7953 (FERM P-4775), ACTT-8005 (FERM P-4776), ACTT-10149 (FERM P-4777), NCA-1503 (FERM P-4778) and SP-43 (FERM P-12754).

The isolation of the thermostable glucokinase gene from the above-described bacteria belonging to the genus Bacillus, the construction of a recombinant DNA containing this gene, the construction of a transformant by using this recombinant DNA, the culture of the transformant, etc. for completing the present invention can each be performed by utilizing known methods, for example, the methods described in Molecular Cloning (Sambrook, J., et. al., Cold Spring Harbor, 1989)

As examples of the vector usable herein, commercially available vectors such as pUC19, pKK223-3, pPL-λ, etc. may be cited. It is preferable to use a vector constructed by combining ori and tac promoters originating in a polycopy vector such as pUC19.

Examples of the host used include *Escherichia coli* strains JM109, TG1, BL21 and N4830-1. It is particularly preferable to use TG1 or BL21 therefor.

The process for producing thermostable glucokinase by using the transformant obtained above may be carried out as follows. First, the transformant is cultured and then the tranformant cells are collected. After lysing the cells with the use of ultrasonic wave, lysozyme, etc. and centrifugation, the supernatant is fractionated by using a commercially available ion exchange resin, an affinity resin or the like. Thus, the thermostable glucokinase can be collected.

The activity of the glucokinase is assayed and indicated by the following methods. Namely, the activity was assayed by mixing 10 μl of an enzyme solution with 1.0 ml of a solution containing 50 mM of a Tris-HCl buffer (pH 9.0), 4 mM of adenosine triphosphate (ATP), 20 mM of magnesium chloride, 0.9 mM of NADP, 12 mM of glucose and 0.5 U of glucose 6-phosphate dehydrogenase (manufactured by Roche Diagnostics) and measuring the initial rate in the change of absorbance at 340 nm at 30° C. The unit of enzyme activity was defined as the amount of the enzyme required in dephosphorylating 1 μmol of ATP per minute under the conditions as defined above.

Now, the present invention will be described in greater detail and in more particularity by reference to the following Examples.

EXAMPLE 1

Analysis of N-terminal Amino Acid Sequence of Glucokinase

The N-terminal amino acid sequence of purified glucokinase was determined by the Edman degradation method. The N-terminal amino acid sequence thus determined is shown by the 1- to 65-positions in the amino acid sequence represented SEQ ID NO:1.

EXAMPLE 2

Construction of DNA Primers

The base sequence of the glucokinase gene encoding the partial amino acid sequence disclosed in Example 1 was presumed. Oligonucleotide probes designed on the basis of this sequence would be in plural forms. In the present invention, oligonucleotides named GKD1 and GKU1, having the base sequences represented by SEQ ID NOS:3 and 4, respectively, were synthesized to order by an outside organization (Amersham Pharmacia Biotech K.K.) and were used as oligonucleotide primers.

EXAMPLE 3

Construction of *Bacillus stearothermophilus* Chromosomal DNA Library 1 g of thermophilic *Bacillus stearothermophilus* UK-563 (FERM P-7275) cells was lysed with lysozyme (manufactured by Seikagaku Kogyo) in accordance with a known method (Saito & Miura, Biochim. Biophys., Acta, vol. 72, p. 619, 1963) and then DNA was extracted with an SDS-containing alkaline buffer and phenol. Further, RNA was degraded with RNase and thus 1 mg of chromosomal DNA was purified.

A 100 μg portion of the obtained chromosomal DNA was partially cleaved with a restriction enzyme Sau3AI (manufactured by Toyobo Co., Ltd.) to give 80 μg of chromosomal DNA fragments. Separately, 1 μg of a vector pUC19 (manufactured by Takara Shuzo Co., Ltd.) was completely cleaved with a restriction enzyme BamHI (manufactured by Toyobo Co., Ltd.) and treated with a bacterium-derived alkali phosphatase (manufactured by Takara Shuzo Co., Ltd.) to thereby give 0.8 μg of vector DNA fragments. Then 0.28 μg of the chromosomal DNA fragments and 0.1 μg of the vector DNA fragments thus obtained were subjected to a ligation by using a T4 phage-derived DNA ligase (manufactured by Takara Shuzo Co., Ltd.) at 16° C. for 30 minutes to give a recombinant DNA. The recombinant DNA thus obtained was mixed with 200 μg of *E. coli* JM109 competent cells (manufactured by Toyobo Co., Ltd.) and allowed to stand on ice for 1 hours. Then the mixture was heated to 42° C. for 120 seconds, thereby conducting transformation.

To the transformant thus obtained, 1 ml of L medium was added and the transformant was cultured at 37° C. for 1 hour. Subsequently, the liquid culture was spread onto an L agar plate medium containing ampicillin. Thus, ampicillin-tolerant strains were obtained. These strains were inoculated into L medium containing 50 μg/ml of ampicillin and cultured therein overnight. After collecting the cells, a plasmid was prepared by the alkali-SDS method to give a *Bacillus stearothermophilus* chromosomal DNA library.

EXAMPLE 4

Isolation of Gene Encoding Thermostable Glucokinase

By using the chromosomal DNA library obtained in Example 3 as a template, gene fractions encoding *Bacillus stearothermophilus* glucokinase were amplified by the PCR method with the use of combinations of two primers capable of amplifying the N-terminal and C-terminal parts of the glucokinase gene, namely, the combination of the primer GKD1 constructed in Example 2 with a primer M13-20 (manufactured by Takara Shuzo Co., Ltd.) and the combination of the primer GKU1 constructed in Example 2 with a primer M13-20 (manufactured by Takara Shuzo Co., Ltd.).

The PCR was carried out by using the liquid reaction mixture having the composition as specified below under the following amplification conditions.
<Composition of Liquid Reaction Mixture>

5 U/100 μl of Taq DNA Polymerase (manufactured by Sawady Technology Co., Ltd.); 10 μl/100 μl of 10-fold concentration Taq DNA Polymerase buffer; 0.01 μg/100 μl of chromosomal DNA (template DNA); 0.2 mM portions of dATP, dTTP, dGTP and dCTP; 1 μM of each primer.
<Amplification Conditions>

(1) 2 minutes at 94° C. (denaturation)

(2) 45 seconds at 94° C. (denaturation)

(3) 30 seconds at 55° C. (annealing)

(4) 2 minutes at 74° C. (reaction)

(Repeating 30 cycles each having the steps (1) to (4).)

Each of the amplified DNA fragments was mixed with a T-vector pT7Blue and subjected to a ligation by using a T4-derived DNA ligase (manufactured by Takara Shuzo Co., Ltd.) at 16° C. for 30 minutes to give a recombinant DNA. The obtained recombinant was mixed with 200 μg of *E. coli* competent cells (manufactured by Toyobo Co., Ltd.), allowed to stand on ice for 1 hour and then heated to 42° C. for 120 seconds, thereby conducting transformation.

To the transformant thus obtained, 1 ml of L medium was added and the transformant was cultured at 37° C. for 1 hour. Subsequently, the liquid culture was spread onto an L agar plate medium containing ampicillin. Thus, ampicillin-tolerant strains were obtained. White colonies among these colonies thus formed were inoculated into L medium containing 50 μg/ml of ampicillin and cultured therein overnight. After collecting the cells, a plasmid was prepared by the alkali-SDS method and the base sequence of the glucokinase structural gene moiety was determined by the dideoxy method.

Based on the base sequence encoding glucokinase determined above, the synthesis of two primers GKD2 and GKU2, designed to amplify the full length gene encoding glucokinase, was ordered to an outside organization (Amersham Pharmacia Biotech K.K.) for use as oligonucleotide primers. The sequence of GKD2 corresponds to the 1- to 21-positions in the base sequence represented by SEQ ID NO:2 in Sequence Listing, while the sequence of GKU2 corresponds to the 932- to 954-positions in the base sequence represented by SEQ ID NO:2 in Sequence Listing. The primer GKD2 was designed with additional CC to its 5'-terminus so as to form a cleavage site for the restriction enzyme NcoI in the N-terminal side of the amplified fragment.

By using the chromosomal DNA obtained in Example 3 as a template, the full-length gene encoding *Bacillus stearothermophilus* glucokinase was amplified by the PCR method with the use of the primers GDK2 and GKU2.

The PCR was carried out by using the liquid reaction mixture having the composition as specified below under the following amplification conditions.
<Composition of Liquid Reaction Mixture>

5 U/100 μl of Taq DNA Polymerase (manufactured by Sawady Technology Co., Ltd.); 10 μl/100 μl of 10-fold concentration Taq DNA Polymerase buffer; 0.01 μg/100 μl of chromosomal DNA (template DNA); 0.2 mM portions of dATP, dTTP, dGTP and dCTP; 1 μM of each primer.
<Amplification Conditions>

(1) 2 minutes at 94° C. (denaturation)

(2) 45 seconds at 94° C. (denaturation)

(3) 30 seconds at 55° C. (annealing)

(4) 2 minutes at 74° C. (reaction)

(Repeating 30 cycles each having the steps (1) to (4).)

The amplified DNA fragment was mixed with a T-vector pT7Blue and subjected to a ligation by using a T4-derived DNA ligase (manufactured by Takara Shuzo Co., Ltd.) at 16° C. for 30 minutes to give a recombinant DNA. The obtained recombinant DNA was mixed with 200 μg of *E. coli* competent cells (manufactured by Toyobo Co., Ltd.), allowed to stand on ice for 1 hour and then heated to 42° C. for 120 seconds, thereby conducting transformation.

To the transformant thus obtained, 1 ml of L medium was added and the transformant was cultured at 37° C. for 1 hours. Subsequently, the liquid culture was spread onto an L agar plate medium containing ampicillin. Thus, ampicillin-tolerant strains were obtained. White colonies among these colonies thus formed were inoculated into L medium containing 50 μg/ml of ampicillin and cultured therein overnight. After collecting the cells, a plasmid was prepared by the alkali-SDS method and the base sequence of the glucokinase structural gene moiety was determined by the dideoxy method. SEQ ID NO:2 in Sequence Listing shows this base sequence.

EXAMPLE 5

Construction of Plasmid Vector for Expression pKK223-3 (manufactured by Amersham Pharmacia Biotech K.K.) was cleaved at the recognition sites of Nae I (enzyme manufactured by Toyobo Co., Ltd.) and Pvu I (enzyme manufactured by Toyobo Co., Ltd.). Then the linear plasmid thus cleaved was separated by agarose gel electrophoresis and DNA fragments containing the Tac promoter were collected. On the other hand, pUC19 (manufactured by Takara Shuzo Co., Ltd.) was cleaved at the recognition site of Eae I (enzyme manufactured by Takara Shuzo Co., Ltd.).

After blunt-ending with a T4 phage-derived DNA polymerase (manufactured by Takara Shuzo Co., Ltd.), it was cleaved at the recognition site of PvuI (enzyme manufactured by Toyobo Co., Ltd.) and the linear plasmid thus cleaved was separated by agarose gel electrophoresis. Then DNA fragments containing ori were collected.

0.1 μg of the above-described Tac promoter-containing DNA fragments were mixed with 0.1 μg of the ori-containing DNA fragments and subjected to a ligation by using a T4 phage-derived DNA ligase (manufactured by Takara Shuzo Co., Ltd.) at 16° C. for 30 minutes. Thus, an expression plasmid vector pUCtac was obtained.

EXAMPLE 6

Construction of Recombinant Vector

The synthesis of an 85 bp DNA represented by SEQ ID NO:5, in which codons corresponding to the 1- to 25-residues in the amino acid sequence represented by SEQ ID NO:1 in Sequence Listing had been substituted by those frequently appearing in *E. coli*, was ordered from an outside organization (Amersham Pharmacia Biotech K.K.). To introduce an NcoI recognition site, 2 cytosine bases were added to the 5'-terminus. This DNA fragment and the plasmid containing the glucokinase gene, obtained in the above-described Example 4, were cleaved at the NcoI recognition site and the ClaI recognition site located at the N-terminus of the glucokinase gene and separated by agarose gel electrophoresis. Thus, DNA fragments containing the N-terminal part and the C-terminal part of the glucokinase gene were obtained respectively from the former and the latter.

0.1 μg portions of these DNA fragments were mixed and subjected to a ligation by using a T4 phage-derived DNA ligase (manufactured by Takara Shuzo Co., Ltd.) at 16° C. for 30 minutes. Thus, a recombinant plasmid pTVOKG containing a thermostable glucokinase gene in which the codons of the N-terminal 25 residues had been optimized for *E. coli* was obtained.

This recombinant plasmid pTVOKG was cleaved at the NcoI recognition site located at the N-terminus of the glucokinase gene to be linear and then blunt-ended with a T4 phage-derived DNA polymerase (manufactured by Takara Shuzo Co., Ltd.). Next, it was further cleaved at the HindIII recognition site located in the C-terminal downstream. The linear plasmid thus cleaved was separated by agarose gel electrophoresis and DNA fragments containing the glucokinase gene were collected. On the other hand, the expression plasmid vector pUCtac obtained in the above-described Example 5 was cleaved at the EcoRI recognition site located 5 bases downstream of the SD sequence to give a linear plasmid. After blunt-ending with an S1 nuclease (manufactured by Takara Shuzo Co., Ltd.), it was further cleaved at the HindIII recognition site in the multicloning site. The linear plasmid thus cleaved was separated by agarose gel electrophoresis and DNA fragments containing the Tac promoter were collected.

0.1 μg of these glucokinase gene-containing DNA fragments were mixed with 0.1 μg of the vector plasmid fragments and subjected to a ligation by using a T4 phage-derived DNA ligase (manufactured by Takara Shuzo Co., Ltd.) at 16° C. for 30 minutes to give a recombinant vector pUtOKGs containing the thermostable glucokinase gene.

This recombinant vector was deposited as a plasmid pUtOKGs with National Institute of Bioscience and Human Technology, Agency of Industrial Science and Technology (Current name: International Patent Organism Depositary, National Institute of Advanced Industrial Science and Technology; Address: AIST Tsukuba Central 6, 1-1, Higashi 1-chome, Tsukuba-shi, Ibaraki-ken 305-8566, Japan) on Nov. 29, 2000 (Accession Number FERM P-18130) and transferred to the deposition under Budapest Treaty on Dec. 17, 2001 (Accession Number FERM BP-7827). FIG. 1 summarizes the procedures for constructing this recombinant vector pUtOKGs.

EXAMPLE 7

Production of Thermostable Glucokinase in *E. coli*

The pUtOGKs constructed in Example 6 was mixed with 200 μg of *E. coli* TG1 competent cells prepared by the calcium method and allowed to stand on ice for 1 hour. Then the mixture was heated to 42° C. for 120 seconds, thereby conducting transformation. To the transformant thus obtained, 1 ml of L medium was added and the transformant was cultured at 37° C. for 1 hour. Subsequently, the liquid culture was spread onto an L agar plate medium containing 50 μg/ml of ampicillin. Thus, 100 *E. coli* colonies containing the thermostable glucokinase gene were obtained and referred to as TG1/pUtOGKs.

The transformant *E. coli* TG1/pUtOGKs was inoculated into 300 ml of L medium containing 50 μg/ml of ampicillin and pre-cultured therein at 37° C. overnight. Next, the liquid pre-culture was inoculated into 20 L of L medium containing 50 μg/ml of ampicillin and cultured therein at 37° C. for 10 hours. Then 1 mM of isopropyl β-thiogalactopyranoside was added and the culturing was continued for additional 15 hours. Next, the cells were collected. The thus collected cells showed 1,000,000 U of glucokinase activity. The cells were suspended in 1000 ml of a 25 mM phosphate buffer (pH 8.0) and ultrasonicated. After removing the disrupted cells, glucokinase was purified from the supernatant by affinity chromatography using Blue-Sepharose and ion exchange chromatography using DEAE-Sepharose. Thus, 360,000 U of glucokinase was recovered, which was 50 times as much as the amount of glucokinase obtained by culturing 20 L *Bacillus stearothermophilus* UK-563 (FERM P-7275).

By examining the properties of the obtained glucokinase, it was found out that this enzyme showed a residual activity of 100% after treating at 60° C. for 1 hour, an optimum pH value of 8.0 and a Km to glucose of 0.1 mM. Based on these results, it was confirmed that the glucokinase obtained according to the process of the present invention had the same properties as the glucokinase originating in *Bacillus stearothermophilus* UK-563 (FERM P-7275).

According to the present invention, thermostable glucokinase can be obtained in a large amount by a convenient process at a low cost.

While the invention has been described in detail and with reference to specific embodiments thereof, it will be apparent to one skilled in the art that various changes and modifications can be made therein without departing from the scope thereof.

This application is based on Japanese patent application No. 2001-006391 filed Jan. 15, 2001, the entire contents thereof being hereby incorporated by reference.

What is claimed is:

1. An isolated polynucleotide encoding a thermostable glucokinase, wherein said thermostable glucokinase comprises amino acids 1 to 317 of SEQ ID NO:1.

2. An isolated polynucleotide encoding a variant of a thermostable glucokinase, wherein said thermostable glucokinase comprises amino acids 1 to 317 of SEQ ID NO:1, and said variant has from 1 to 20 amino acid changes in SEQ ID NO:1 selected from the group consisting of deletions, substitutions or additions, and wherein said variant has thermostable glucokinase activity.

3. An isolated polynucleotide encoding a thermostable glucokinase, wherein said polynucleotide comprises nucleotides 1 to 954 of SEQ ID NO:2.

4. An isolated polynucleotide encoding a variant of a thermostable glucokinase, wherein said polynucleotide comprises nucleotides 1 to 954 of SEQ ID NO:2, wherein said polynucleotide has from 1 to 60 nucleotide changes selected from the group consisting of deletions, substitutions or additions, and wherein said polynucleotide encodes a polypeptide with thermostable glucokinase activity.

5. An isolated polynucleotide selected from the group consisting of:
   (a) an isolated polynucleotide that encodes a polypeptide comprising amino acids 1 to 317 of SEQ ID NO:1, and
   (b) an isolated polynucleotide comprising nucleotides 1 to 954 of SEQ ID NO:2.

6. A recombinant vector comprising a polynucleotide of any one of claims 1 to 5.

7. A host cell transformed with the recombinant vector as claimed in claim 6.

8. A process for producing a thermostable glucokinase, which comprises (a) culturing a host cell as claimed in claim 7 under conditions such that said host cell expresses said thermostable glucokinase, and (b) collecting the thermostable glucokinase so expressed.

* * * * *